(12) United States Patent
Blackwell et al.

(10) Patent No.: US 7,727,233 B2
(45) Date of Patent: Jun. 1, 2010

(54) SPINOUS PROCESS STABILIZATION DEVICES AND METHODS

(75) Inventors: Jonathan Blackwell, Cordova, TN (US); Aurelien Bruneau, Memphis, TN (US)

(73) Assignee: Warsaw Orthopedic, Inc.

( * ) Notice: Subject to any disclaimer, the term of this patent is extended or adjusted under 35 U.S.C. 154(b) by 105 days.

(21) Appl. No.: 11/117,809

(22) Filed: Apr. 29, 2005

(65) Prior Publication Data
US 2006/0247640 A1 Nov. 2, 2006

(51) Int. Cl.
*A61B 17/58* (2006.01)
(52) U.S. Cl. ............... 606/71; 606/251; 606/252; 606/253
(58) Field of Classification Search ........... 606/61, 606/246–260, 70, 71; 623/17.11, 16.11, 623/17.15–17.16; 403/53, 54, 58, 59, 68, 403/73, 84
See application file for complete search history.

(56) References Cited

U.S. PATENT DOCUMENTS

| | | | |
|---|---|---|---|
| 2,677,369 A | | 5/1954 | Knowles |
| 2,774,350 A | | 12/1956 | Cleveland, Jr. |
| 3,648,691 A | | 3/1972 | Lumb et al. |
| 3,693,616 A | | 9/1972 | Roaf et al. |
| 4,011,602 A | | 3/1977 | Rybicki et al. |
| 4,257,409 A | | 3/1981 | Bacal et al. |
| 4,433,677 A | * | 2/1984 | Ulrich et al. ............... 606/250 |
| 4,554,914 A | | 11/1985 | Kapp et al. |
| 4,573,454 A | | 3/1986 | Hoffman |
| 4,604,995 A | | 8/1986 | Stephens et al. |
| 4,686,970 A | | 8/1987 | Dove et al. |
| 4,827,918 A | | 5/1989 | Olerud |
| 5,011,484 A | | 4/1991 | Breard |
| 5,047,055 A | | 9/1991 | Bao et al. |
| 5,092,866 A | | 3/1992 | Breard et al. |
| 5,201,734 A | | 4/1993 | Cozad et al. |
| 5,306,275 A | | 4/1994 | Bryan |
| 5,360,430 A | | 11/1994 | Lin |
| 5,366,455 A | * | 11/1994 | Dove et al. ............... 606/61 |
| 5,415,661 A | | 5/1995 | Holmes |
| 5,437,672 A | | 8/1995 | Alleyne |
| 5,439,463 A | * | 8/1995 | Lin ............... 606/61 |
| 5,454,812 A | | 10/1995 | Lin |
| 5,458,641 A | * | 10/1995 | Ramirez Jimenez ..... 623/17.11 |
| 5,496,318 A | | 3/1996 | Howland et al. |

(Continued)

FOREIGN PATENT DOCUMENTS

DE 2821678 A1 11/1979

(Continued)

OTHER PUBLICATIONS

Posterior Spinal Instrumentation for Thoracolumbar Tumor and Trauma Reconstruction, Seminars in Spine Surgery, vol. 9, No. 3, Sep. 1997, pp. 260-277.

(Continued)

*Primary Examiner*—Eduardo C Robert
*Assistant Examiner*—Tara R George

(57) ABSTRACT

Devices and methods for supporting adjacent spinous processes include opposing plates movable toward one another along a cross post to contact opposite sides of each of the spinous processes, and a spacer member about the cross post contacting the adjacent surfaces of the spinous processes to resist movement of the spinous processes toward one another under spinal extension motion.

21 Claims, 9 Drawing Sheets

U.S. PATENT DOCUMENTS

| | | | |
|---|---|---|---|
| 5,609,634 A | | 3/1997 | Voydeville |
| 5,628,756 A | | 5/1997 | Barker, Jr. et al. |
| 5,645,599 A | | 7/1997 | Samani |
| 5,674,295 A | | 10/1997 | Ray et al. |
| 5,676,702 A | | 10/1997 | Ratron |
| 5,690,649 A | | 11/1997 | Li |
| 5,702,452 A | | 12/1997 | Argenson et al. |
| 5,725,582 A | | 3/1998 | Bevan et al. |
| 5,810,815 A | | 9/1998 | Morales |
| 5,836,948 A | | 11/1998 | Zucherman et al. |
| 5,860,977 A | | 1/1999 | Zucherman et al. |
| 5,888,223 A | * | 3/1999 | Bray, Jr. ............... 623/17.16 |
| 5,976,186 A | | 11/1999 | Bao et al. |
| 5,980,523 A | * | 11/1999 | Jackson ................... 606/252 |
| 6,022,376 A | | 2/2000 | Assell et al. |
| 6,048,342 A | | 4/2000 | Zucherman et al. |
| 6,068,630 A | | 5/2000 | Zucherman et al. |
| 6,132,464 A | | 10/2000 | Martin |
| 6,139,548 A | * | 10/2000 | Errico ...................... 606/252 |
| 6,235,030 B1 | * | 5/2001 | Zucherman et al. ........... 606/61 |
| 6,261,586 B1 | * | 7/2001 | McKay ...................... 424/423 |
| 6,293,949 B1 | | 9/2001 | Justis et al. |
| 6,312,431 B1 | | 11/2001 | Asfora |
| 6,352,537 B1 | | 3/2002 | Strnad |
| 6,364,883 B1 | | 4/2002 | Santilli |
| 6,402,750 B1 | | 6/2002 | Atkinson et al. |
| 6,440,169 B1 | | 8/2002 | Elberg et al. |
| 6,451,019 B1 | | 9/2002 | Zucherman et al. |
| 6,500,178 B2 | | 12/2002 | Zucherman et al. |
| 6,582,433 B2 | | 6/2003 | Yun |
| 6,626,944 B1 | | 9/2003 | Taylor |
| 6,645,207 B2 | | 11/2003 | Dixon et al. |
| 6,695,842 B2 | * | 2/2004 | Zucherman et al. ........... 606/61 |
| 6,709,435 B2 | | 3/2004 | Lin |
| 6,723,126 B1 | | 4/2004 | Berry |
| 6,733,534 B2 | | 5/2004 | Sherman |
| 6,761,720 B1 | | 7/2004 | Senegas |
| 6,835,205 B2 | | 12/2004 | Atkinson et al. |
| 6,946,000 B2 | | 9/2005 | Senegas et al. |
| 7,041,136 B2 | | 5/2006 | Goble et al. |
| 7,048,736 B2 | * | 5/2006 | Robinson et al. ............... 606/61 |
| 7,087,083 B2 | | 8/2006 | Pasquet et al. |
| 7,163,558 B2 | | 1/2007 | Senegas et al. |
| 7,201,751 B2 | | 4/2007 | Zucherman et al. |
| 7,238,204 B2 | | 7/2007 | Le Couedic et al. |
| 7,306,628 B2 | | 12/2007 | Zucherman et al. |
| 7,335,203 B2 | * | 2/2008 | Winslow et al. ............. 606/249 |
| 7,377,942 B2 | | 5/2008 | Berry |
| 7,442,208 B2 | | 10/2008 | Mathieu et al. |
| 7,445,637 B2 | | 11/2008 | Taylor |
| 2002/0143331 A1 | | 10/2002 | Zucherman et al. |
| 2002/0183746 A1 | * | 12/2002 | Zucherman et al. ........... 606/61 |
| 2003/0040746 A1 | * | 2/2003 | Mitchell et al. ................ 606/61 |
| 2003/0065330 A1 | * | 4/2003 | Zucherman et al. ........... 606/61 |
| 2003/0153914 A1 | * | 8/2003 | Oribe et al. ................... 606/61 |
| 2003/0153915 A1 | | 8/2003 | Nekozuka et al. |
| 2003/0216736 A1 | | 11/2003 | Robinson et al. |
| 2004/0097931 A1 | | 5/2004 | Mitchell |
| 2004/0106995 A1 | | 6/2004 | Le Couedic et al. |
| 2004/0181282 A1 | | 9/2004 | Zucherman et al. |
| 2005/0010293 A1 | | 1/2005 | Zucherman et al. |
| 2005/0049708 A1 | | 3/2005 | Atkinson et al. |
| 2005/0143822 A1 | * | 6/2005 | Paul ....................... 623/17.16 |
| 2005/0165398 A1 | | 7/2005 | Reiley |
| 2005/0203512 A1 | * | 9/2005 | Hawkins et al. ................ 606/61 |
| 2005/0203624 A1 | | 9/2005 | Serhan et al. |
| 2005/0216082 A1 | * | 9/2005 | Wilson et al. ............. 623/17.11 |
| 2005/0228391 A1 | | 10/2005 | Levy et al. |
| 2005/0261768 A1 | | 11/2005 | Trieu |
| 2005/0288672 A1 | | 12/2005 | Ferree |
| 2006/0004447 A1 | | 1/2006 | Mastrorio et al. |
| 2006/0015181 A1 | | 1/2006 | Elberg |
| 2006/0064165 A1 | | 3/2006 | Zucherman et al. |
| 2006/0084983 A1 | | 4/2006 | Kim |
| 2006/0084985 A1 | | 4/2006 | Kim |
| 2006/0084987 A1 | | 4/2006 | Kim |
| 2006/0084988 A1 | | 4/2006 | Kim |
| 2006/0085069 A1 | | 4/2006 | Kim |
| 2006/0085070 A1 | | 4/2006 | Kim |
| 2006/0085074 A1 | | 4/2006 | Raiszadeh |
| 2006/0089654 A1 | | 4/2006 | Lins et al. |
| 2006/0089719 A1 | | 4/2006 | Trieu |
| 2006/0106381 A1 | | 5/2006 | Ferree et al. |
| 2006/0106397 A1 | | 5/2006 | Lins |
| 2006/0111728 A1 | | 5/2006 | Abdou |
| 2006/0122620 A1 | | 6/2006 | Kim |
| 2006/0136060 A1 | | 6/2006 | Taylor |
| 2006/0184247 A1 | | 8/2006 | Edidin et al. |
| 2006/0184248 A1 | | 8/2006 | Edidin et al. |
| 2006/0195102 A1 | | 8/2006 | Malandain |
| 2006/0217726 A1 | | 9/2006 | Maxy et al. |
| 2006/0235387 A1 | | 10/2006 | Peterman |
| 2006/0235532 A1 | | 10/2006 | Meunier et al. |
| 2006/0241613 A1 | | 10/2006 | Bruneau et al. |
| 2006/0247623 A1 | | 11/2006 | Anderson et al. |
| 2006/0247640 A1 | | 11/2006 | Blackwell et al. |
| 2006/0264938 A1 | | 11/2006 | Zucherman et al. |
| 2006/0271044 A1 | | 11/2006 | Petrini et al. |
| 2006/0271049 A1 | | 11/2006 | Zucherman et al. |
| 2006/0293662 A1 | | 12/2006 | Boyer, II et al. |
| 2006/0293663 A1 | | 12/2006 | Walkenhorst et al. |
| 2007/0043362 A1 | | 2/2007 | Malandain et al. |
| 2007/0162000 A1 | | 7/2007 | Perkins |
| 2007/0198091 A1 | | 8/2007 | Boyer et al. |
| 2007/0233068 A1 | | 10/2007 | Bruneau et al. |
| 2007/0233081 A1 | | 10/2007 | Pasquet et al. |
| 2007/0233089 A1 | | 10/2007 | DiPoto et al. |
| 2007/0270834 A1 | | 11/2007 | Bruneau et al. |
| 2008/0161818 A1 | | 7/2008 | Kloss et al. |

FOREIGN PATENT DOCUMENTS

| | | |
|---|---|---|
| EP | 0322334 B1 | 2/1992 |
| EP | 1138268 A1 | 10/2001 |
| EP | 1330987 A1 | 7/2003 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2799948 A1 | 4/2001 |
| FR | 2816197 A1 | 5/2002 |
| GB | 780652 | 8/1957 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | WO 2005/009300 A1 | 2/2005 |
| WO | WO 2005/044118 A1 | 5/2005 |
| WO | WO 2005/110258 A1 | 11/2005 |
| WO | WO 2006/064356 A1 | 6/2006 |

WO WO 2007/034516 A1 3/2007

OTHER PUBLICATIONS

Reduction and Fixation of Late Diagnosed Lower Cervical Spine Dislocations Using Daab Plate, Archives of Orthopaedic and Traumatic Surgery, 1984, pp. 353-355.

Posterior Spinal Fusion Using Internal Fixation with the Daab Plate, Act. Orthop. Scand. 55, pp. 310-314, 1984.

The Value of the Wilson Plate in Spinal Fusion, M.C. Cobey, M.D., May 1971.

"Dispositivo Intervertebrale Ammortizzante DIAM," date unknown, p. 1.

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumber Spine," date unknown, pp. 1-24, Spine Next, An Abbott Laboratories Company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: A Biomechanical Study and Clinical Experience Based on 82 Cases," Eur. Spine J., Oct. 2002, pp. S192-S197, vol. 11, Suppl.2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: The Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sept. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopedique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'Arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: The Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5émes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

* cited by examiner

SPINOUS PROCESS STABILIZATION DEVICES AND METHODS

BACKGROUND

Spinal stabilization procedures are performed and include placement of devices between vertebral bodies in the disc space or along the spinal column. For example, varieties of inter-body fusion devices are widely used following partial or total discectomies to fuse adjacent vertebrae. Artificial disc devices can be placed in the disc space if motion preservation is desired. Still other stabilization devices contemplate the attachment of plates, rods or tethers extradiscally along the vertebrae. Still others are positioned between spinous processes. One example is shown in U.S. Patent Application Publication No. 2003/0216736, which is incorporated herein by reference. There remains a need for devices for spinal stabilization through attachment to the spinous processes along one or more vertebral levels.

SUMMARY

Devices and methods for supporting adjacent spinous processes include opposing plates movable toward one another along a cross post to contact opposite sides of each of the spinous processes, and a member about the cross post contacting the adjacent surfaces of the spinous processes to resist movement of the spinous processes toward one another under spinal extension motion.

According to one aspect, there is provided an implantable device for stabilization of spinous processes. The device includes first and second spaced plates, the first plate having a surface facing a surface of the second plate. A post connected to each of the plates extends from the facing surface of the first plate to the facing surface of the second plate. The connection of the post to the second plate can be adjustable to enable a change of spacing between the first plate and the second plate. A spacer member can be non-rotatably positioned about the post. The spacer member is sized to extend between and contact adjacent surfaces of the spinous processes.

In another aspect, an implantable device for stabilization of spinous processes includes first and second spaced plates each having clamping surfaces facing one another. A post is connected to each of the plates and extends from and is pivotal relative to the clamping surface of the first plate. The connection of the post to the second plate is adjustable to enable changing the spacing between the first plate and the second plate. A spacer member can be positioned about the post. The spacer member is sized to extend between and contact adjacent superior and inferior surfaces of the spinous processes with the clamping surfaces positioned against opposite sides of the spinous processes.

According to another aspect, a method for stabilizing spinous processes of a spinal column comprises: selecting a spacer member from a set of spacer members, the selected spacer member providing a desired fit between adjacent spinous processes; engaging a first plate along a first side of the adjacent spinous processes; positioning the spacer member along a post extending from the first plate and between the adjacent spinous processes, the spacer member extending between and limiting extension movement of the adjacent spinous processes; and engaging a second plate along a second side of the adjacent spinous process with the spacer member between the first and second plates.

These and other aspects will be discussed further below.

DESCRIPTION OF THE ILLUSTRATED EMBODIMENTS

Figure 1:
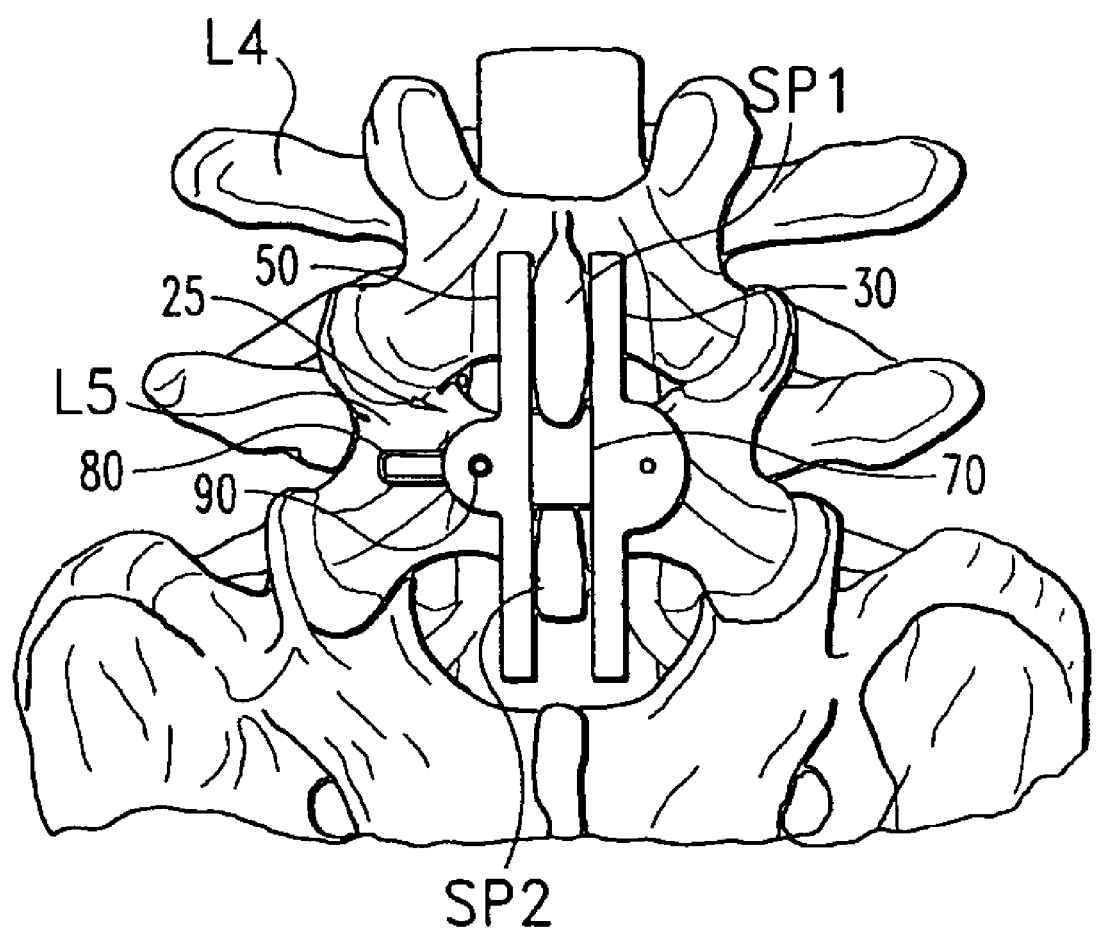
FIG. 1 is a posterior view of a portion of the spine with a device positioned between adjacent spinous processes.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Figure 2:
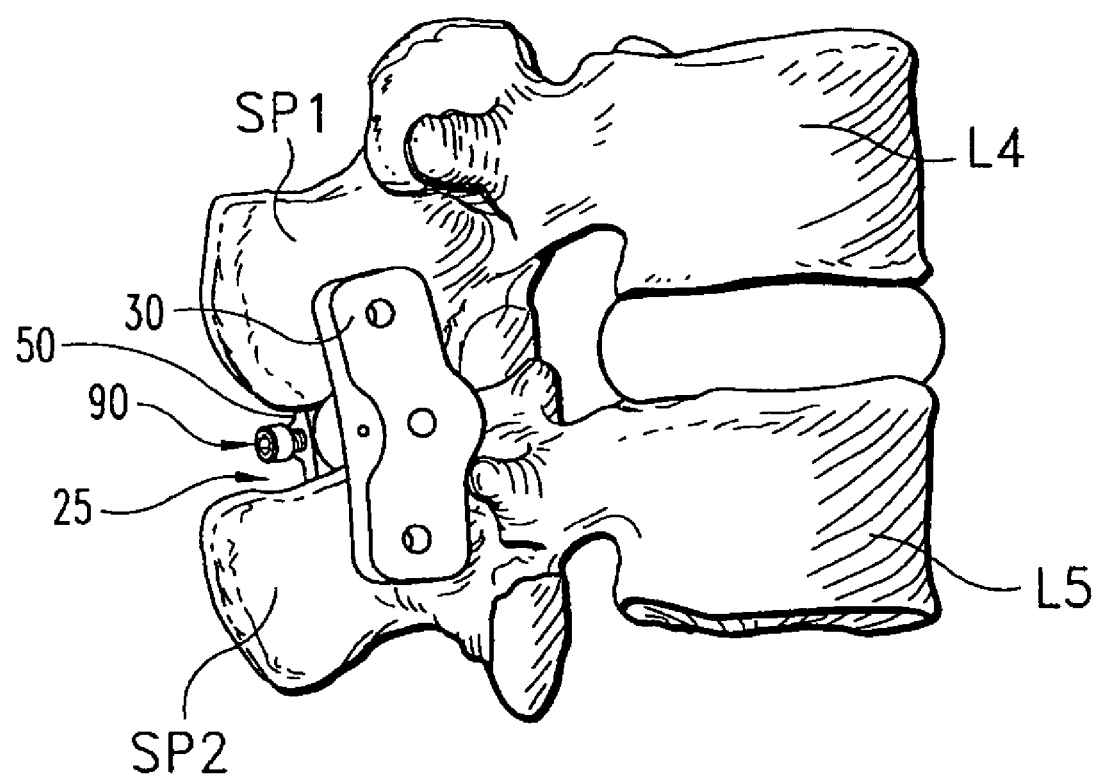
FIG. 2 is a laterally oriented view of the device and spine portion of FIG. 1.

In FIGS. 1 and 2 there is shown a device 25 engaged to the spinal processes SP1 and SP2 of the L4 and L5 vertebrae. While vertebrae L4 and L5 are shown, it is contemplated that device 25 can be engaged to adjacent spinous processes at any vertebral level of the spinal column. The device may also be adapted to extend along multiple vertebral levels, and it is also contemplated that individual devices may be employed at multiple vertebral levels.

Device 25 includes a first plate 30, a second plate 50 and a spacer member 70 therebetween. First and second plates 30, 50 are movable toward one another along a cross post 80 into clamping engagement with spinous processes SP1, SP2. Locking member 90 can engage cross post 80 to maintain a desired relative positioning between first and second plates 30, 50. A spacer member 70 is positioned along cross post 80, and extends between adjacent super and inferior surfaces of the spinous processes SP1 and SP2.

Engagement of plates 30, 50 to the spinous processes SP1, SP2 resists movement of the spinous processes SP1, SP2 toward and away from one another as a result of spinal extension and flexion, respectively, or as a result of any other movement or condition. Spacer member 70 extends between plates 30, 50 and also between spinous processes SP1, SP2 to resist movement of the spinous processes toward one another as a result of spinal extension. Spacer member 70 can also provide support of the vertebrae to maintain or provide postoperative distraction between the spinous processes SP1 and SP2.

Figure 3:
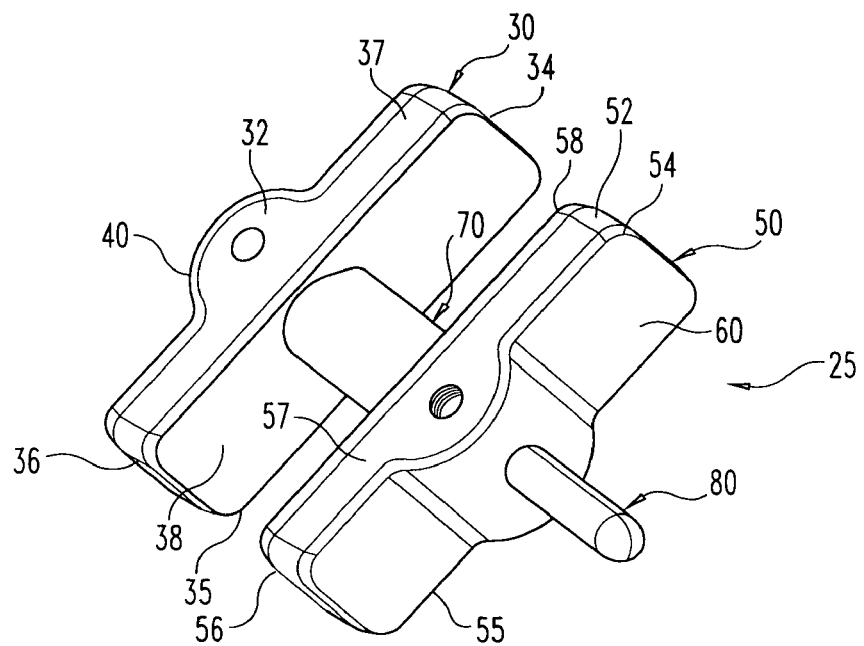
FIG. 3 is a perspective view of the device of FIG. 1.

A perspective view of device 25 is shown in FIG. 3 with plates 30, 50 switched in positioning relative to their orientation in FIGS. 1 and 2, and also with cross post 80 extending in the opposite direction from its FIG. 1 direction. In addition, locking member 90 is removed. First plate 30 includes an elongated body 32 extending between a cephalad end 34 and a caudal end 36, and also between an anterior side 35 and a posterior side 37. Body 32 can be rounded about ends 34, 36 and also sides 35, 37 to remove any abrupt transitions between surfaces that may contact and cause irritation in adjacent tissue and/or neural elements.

First plate 30 further includes a clamping surface 38 and an opposite outer surface 40. Clamping surface 38 is positionable against the sides of the respective adjacent spinous processes SP1 and SP2 to provide frictional engagement therewith. As discussed further below, cross post 80 includes one end secured to first plate 30 and extends transversely thereto from clamping surface 38 toward second plate 50.

Second plate 50 is positioned about and movable along cross post 80 and securable in position thereto with locking member 90. Second plate 50 includes an elongated body 52 extending between a cephalad end 54 and a caudal end 56, and also between an anterior side 55 and a posterior side 57. Body 52 can be rounded about ends 54, 56 and also sides 55, 57 to remove any abrupt transitions between surfaces that may contact and irritate adjacent tissue and/or neural elements.

Figure 4:
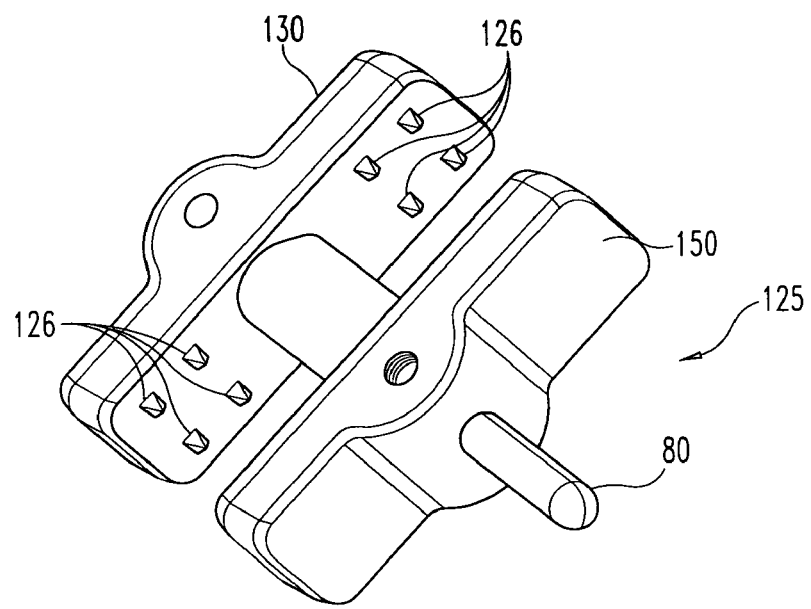
FIG. 4 is a perspective view of another embodiment device.

Second plate 50 further includes a clamping surface 58 and an opposite outer surface 60. Clamping surface 58 is positionable against the sides of the respective adjacent spinous processes SP1 and SP2 to provide frictional engagement therewith. In another embodiment, a substantially similar spinous process stabilization device 125 is shown in FIG. 4. In device 125, spikes 126 extend from a clamping surface of first plate 130 to embed in the bony structure of the spinous processes. In another embodiment device 125 shown in FIG. 4, spikes (not shown in second plate 150) extend from a clamping surface of second plate 150 to embed in the bony structure of the spinous processes. Other surface treatments are also contemplated, including ridges, knurlings, peaks and valleys, teeth, and etchings, for example.

Figure 5:
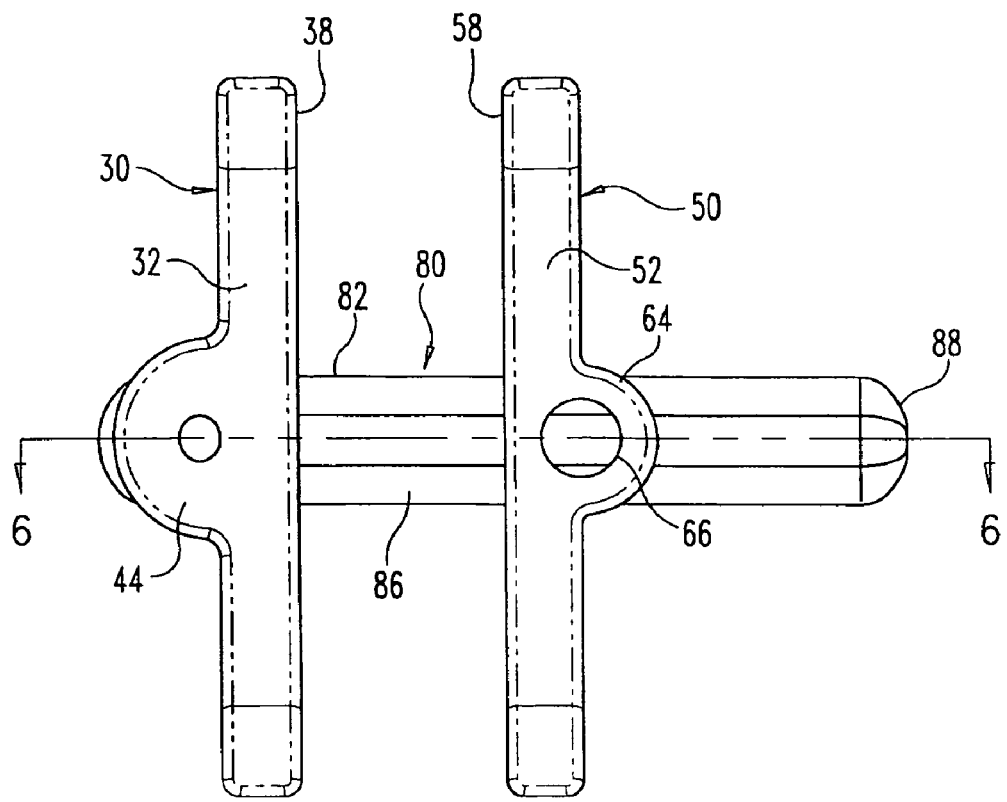
FIG. 5 is an elevation view of the device with the central spacer member removed.
Figure 6:
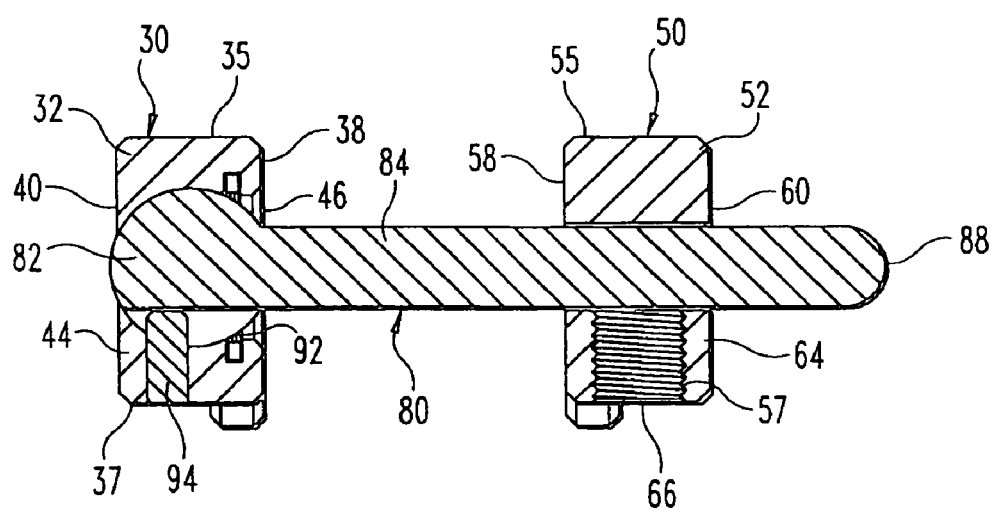
FIG. 6 is a section view along line 6-6 of FIG. 5.
Figure 7:
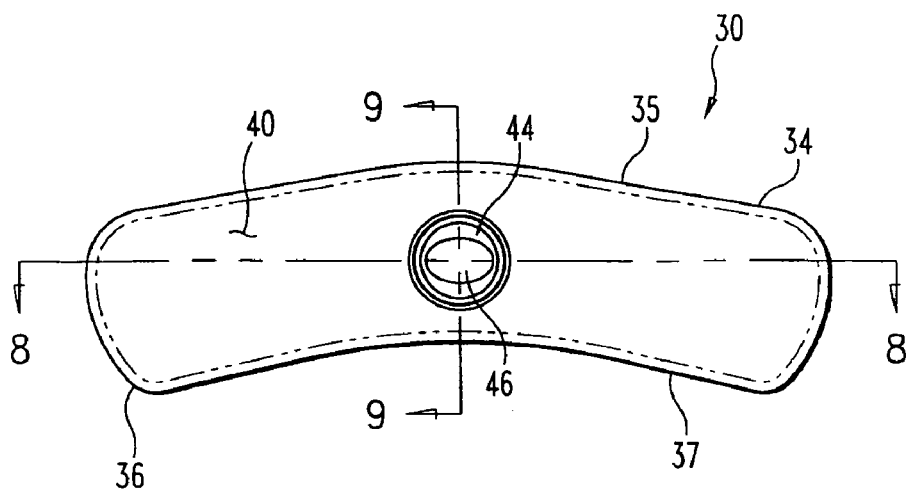
FIG. 7 is an elevation view of a first plate comprising a portion of the device.
Figure 8:
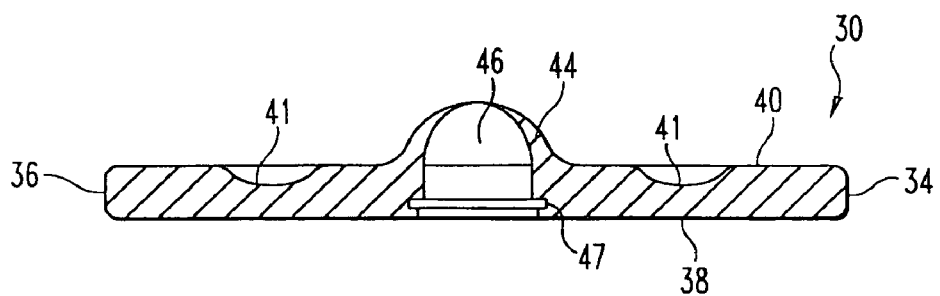
FIG. 8 is a section view along line 8-8 of FIG. 7.
Figure 9:
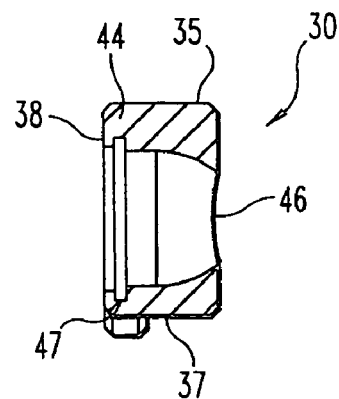
FIG. 9 is a section view along line 9-9 of FIG. 7.

Device 25 is further shown in FIGS. 5 and 6 without spacer member 70. First plate 30, shown in isolation in FIGS. 7-9, includes a central receiving portion 44 that defines a receptacle 46 that receives a head 82 of cross post 80 therein. A retaining member 92 is received in circumferential groove 47 and extends about receptacle 46 and the underside of head 82 to capture head 82 in receptacle 46. In one embodiment, head 82 is pivotal in receptacle 46, allowing various angular positions of an elongated shaft 84 extending through retaining member 92 from head 82 to a terminal end 88. The underside of head 82 can be seated upon retaining member 92 to prevent plates 30, 50 from moving away from one another. Retaining member 92 can be in the form of a C-shaped ring or any other form suitable to retain head 82 in receptacle 46.

Figure 13:
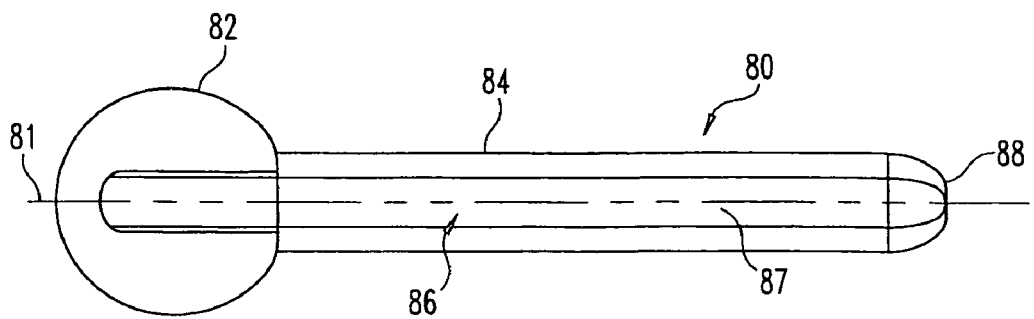
FIG. 13 is an elevation view of a cross post comprising a portion of the device.
Figure 14:
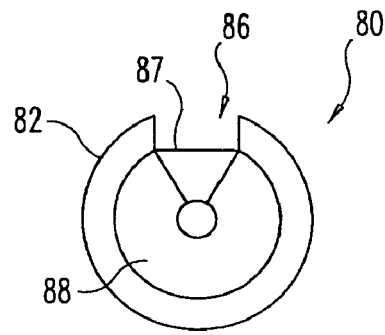
FIG. 14 is an end view of the cross post of FIG. 13.

As further shown in FIGS. 13-14, cross post 80 includes a keyway 86 extending therealong from head 82 to terminal end 88. Keyway 86 forms a channel at least in head 82 to receive pin 94 and resist cross post 80 from rotating about its longitudinal axis 81 in receptacle 46. Keyway 86 includes a flat surface portion 87 along shaft 84 that extends from head 82 to a terminal end 88. In another form, shaft 84 of cross post 80 includes a circular cross-section with no keyway therealong. Such an embodiment may be employed, for example, when it is desired to employ spacer members rotatable about cross post 80, as discussed further below.

Figure 10:
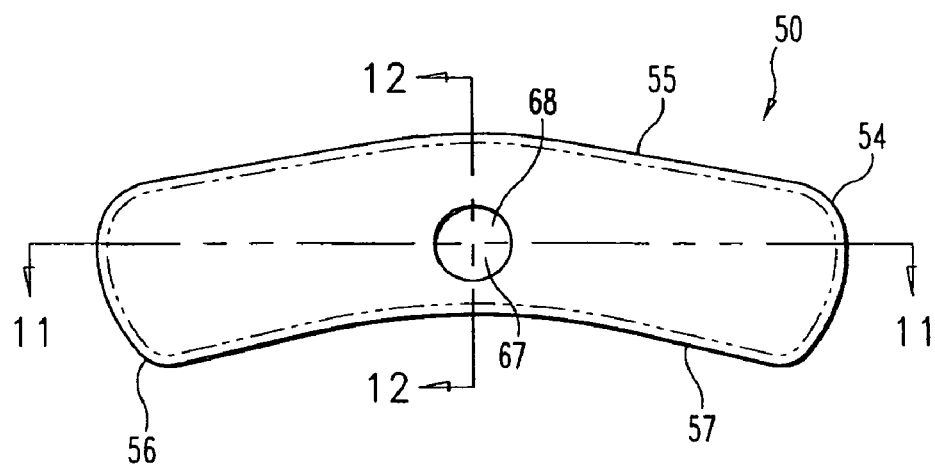
FIG. 10 is an elevation view of a second plate comprising a portion of the device.
Figure 11:
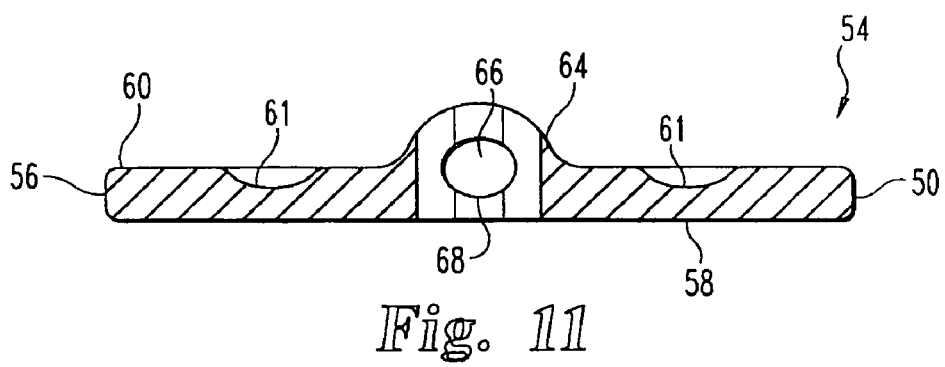
FIG. 11 is a section view along line 11-11 of FIG. 10.
Figure 12:
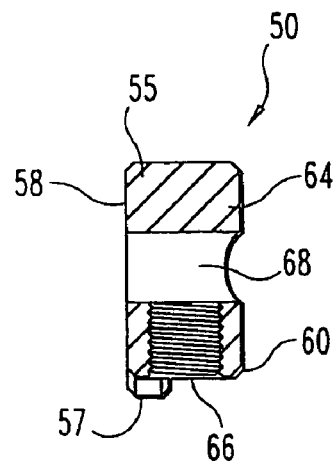
FIG. 12 is a section view along line 12-12 of FIG. 10.

Second plate 50, shown in isolation in FIGS. 10-12, includes a central receiving portion 64 that defines a receptacle 66 in communication with a through-bore 68. Through-bore 68 extends between and opens at clamping surface 58 and outer surface 60. Receptacle 66 is formed through central receiving portion 64 and is in communication with through-bore 68 and opens at posterior side 57. In the illustrated embodiment, receptacle 66 is threaded and threadingly engages an externally threaded locking member 90. Locking member 90 is movable along receptacle 66 into and out of engagement with keyway 86 of cross post 80 to secure second plate 50 in a desired position and relative spacing from first plate 30 along cross post 80.

Post 80 is positionable through through-bore 68 to allow securement of second plate 50 thereto. In the illustrated embodiment, through-bore 68 includes a keypath 67 that interacts with keyway 86 to prevent second plate 50 from rotating about cross post 80. The flats on the cross post 80 and through-bore 68 are interruptions in the circular form of the post and bore that interfit to prevent plate 50 from rotating. The post and bore could be of some other cross sectional shape providing a slip fit but avoiding rotation of the locking plate relative to the post. For example, polygonal or interdigitating key and key-way shapes could be used.

First and second plates 30, 50 can be curved between their respective upper and lower ends. For example, anterior sides 35, 55 are convexly curved to provide an anatomical fit between the spinous processes. Concavely curved posterior sides 37, 57 minimize posterior protrusion of plates 50, 70 in the region between the spinous process. Outer surfaces 40, 60 of first and second plates 30, 50 can further include reliefs 41, 61 to facilitate placement and retention of ends of a compression tool (not shown) that is operable to apply a compression force to move the plates into clamping engagement on the spinal processes.

The central receiving portions 44, 64 of plates 30, 50 provide an area of increased thickness of the plates to accommodate attachment of the respective portions of the cross post 80 and locking member 90. Other embodiments contemplate that the plates 30, 50 have a constant thickness along their respective lengths. In other embodiments, the plates 30, 50 may include longitudinal ribs to increase stiffness, or through holes to allow attachment of tethering or other supplemental spinal stabilization or attachment devices.

Figure 15:
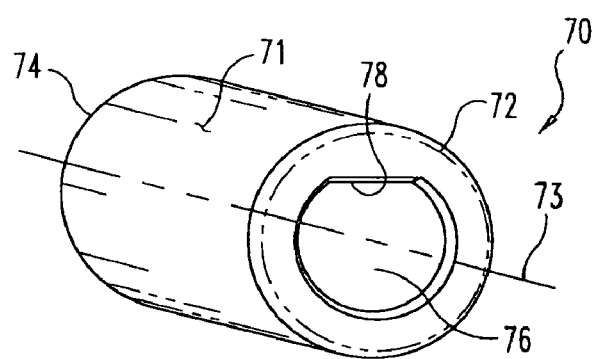
FIG. 15 is a perspective view of one embodiment spacer member.

Various embodiments of spacer members are shown in FIGS. 15-21. In FIG. 15 spacer member 70 includes a cylindrical body extending along a longitudinal axis 73. The body includes an outer surface 71 defining a circular shape in cross-section when viewed orthogonally to axis 73. A passage 76 extends along axis 73 between opposite ends 72, 74 and is sized and shaped to slidably receive cross post 80 therethrough. A keyed portion 78 is provided along one side of passage 76 that is positionable in contact with keyway 86 of cross post 80. Keyed portion 78 interacts with keyway 86 to prevent spacer member 70 from rotating about cross post 80.

Figure 16:
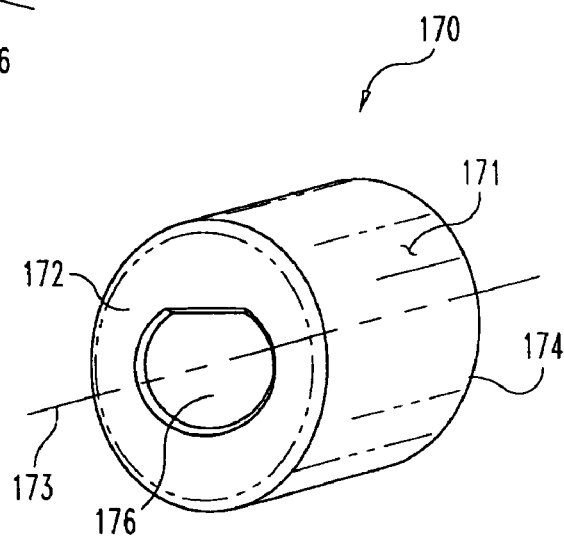
FIG. 16 is a perspective view of another embodiment spacer member.

In FIG. 16 another embodiment spacer member 170 is provided that is similar to spacer member 70 and includes a cylindrical body extending along longitudinal axis 173 between opposite ends 172, 174. The body includes an outer surface 171 extending thereabout that defines an oval shape in cross-section orthogonally to longitudinal axis 173. A passage 176 extends along axis 173 and is sized and shaped to slidingly receive cross post 80 therein. The elongated or maximum height portions of the oval can be oriented toward the respective inferior and superior spinous process surfaces. This orients the reduced width portion of the oval shape in the anterior-posterior direction to minimize intrusion into the adjacent tissue while maximizing the height between the spinous processes.

Figure 17:
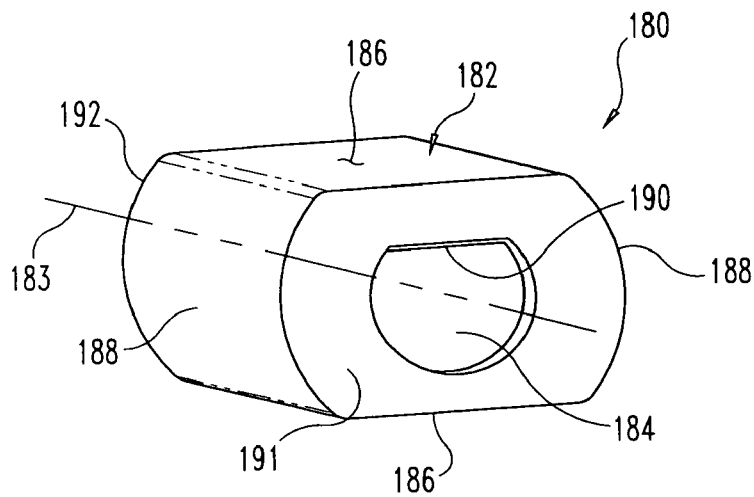
FIG. 17 is a perspective view of another embodiment spacer member.

FIG. 17 shows another embodiment spacer member 180 having a cylindrical body 182 extending along a longitudinal axis 183. The body includes a generally rectangular outer surface profile in cross-section viewed orthogonally to longitudinal axis 183. A passage 184 extends along axis 183 between opposite flat ends 191, 192. The outer surface profile includes convexly curved anterior and posterior walls 188 extending between planar upper and, lower surfaces 186. Passage 184 can include a keyed portion 190 to prevent rotation of spacer member 180 about cross post 80 and to ensure proper alignment during assembly.

Figure 18:
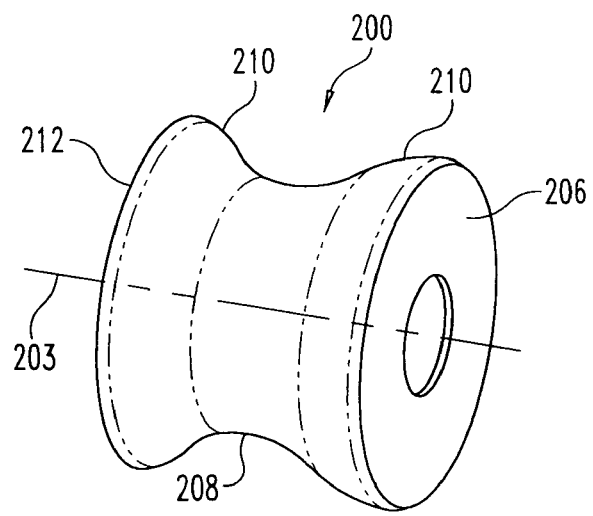
FIG. 18 is a perspective view of another embodiment spacer member.

FIG. 18 shows another embodiment spacer member 200 having a cylindrical body extending along longitudinal axis 203. The body includes an outer shape in the form of an hourglass extending along longitudinal axis 203. A passage 204 extends along axis 203 between opposite flat ends 206, 212 to receive cross post 80. A concavely curved outer surface portion 208 extends between raised ends 210. The spinous processes are positionable in concavely curved outer surface portion 208 and received between raised ends 210. The nested arrangement provides increased surface area of contact between spacer member 200 and the spinous processes, distributing loading exerted on the spinous processes over correspondingly greater surface areas.

Figure 19:
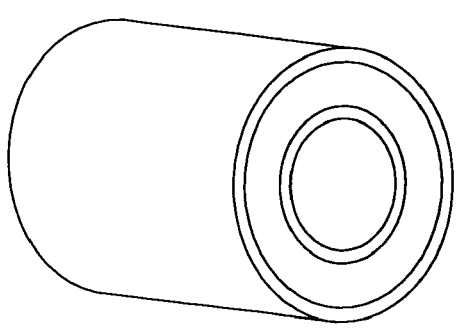
FIG. 19 is a perspective view of another embodiment spacer member.
Figure 20:
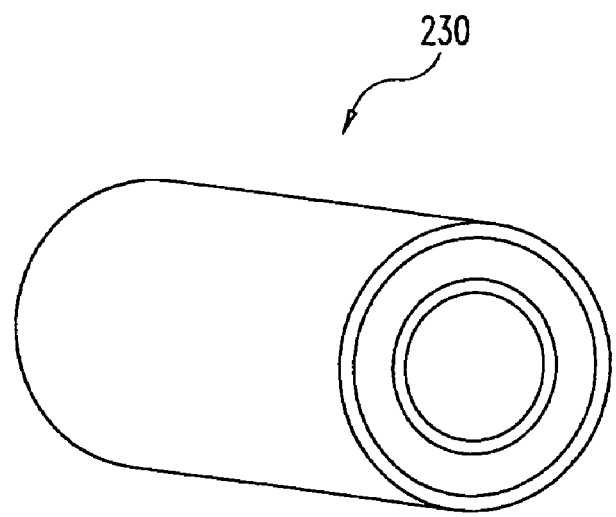
FIG. 20 is a perspective view of another embodiment spacer member.

FIGS. 19 and 20 show spacer member 220, 230 that are similar to the spacer members 70, 170 of FIGS. 15 and 16, respectively. However, the passages do not include a keyed portion, allowing the spacer members 220, 230 to rotate about cross post 80. It is also contemplated that the spacer member embodiments 180 and 200 in FIGS. 17 and 18 can have passages with keyed portions or without keyed portions, depending whether or not it is desired to have the spacer member rotatable about the cross post 80. The rotatable spacer members facilitate the spacer member maintaining a bearing relationship with the adjacent spinous process surfaces without twisting or binding as the spinous processes move relative to the spacer member.

Figure 21:
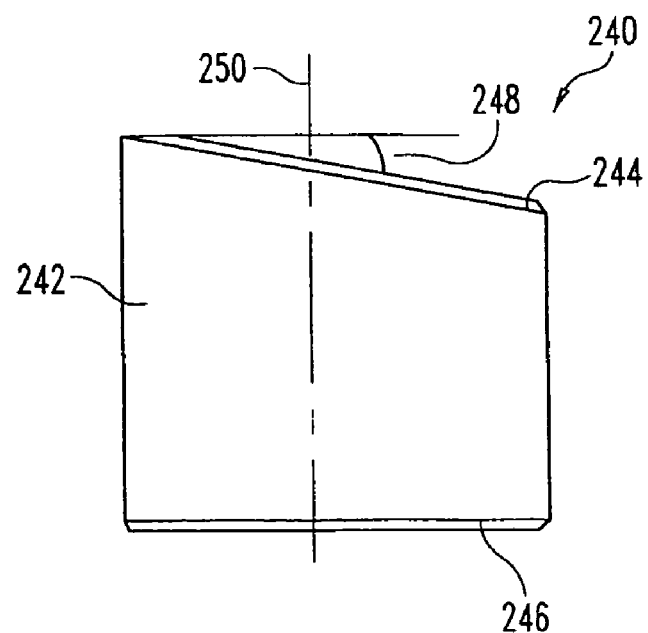
FIG. 21 is an elevation view of another embodiment spacer member.

FIG. 21 shows a spacer member 240 having a cylindrical body 242 extending between a first end 244 and a second end 246. A passage (not shown) can be provided along spacer member 240 between ends 244, 246. End 244 can be angled relative to central axis 250 at an angle 248. Spacer member 240 with the angled end can be employed in procedures where one of the plates 30, 50 is angled relative to the other to accommodate the spinous process anatomy. The angled end or ends can conform to and maintain contact with the clamping surfaces or surfaces of the plate or plates. Such contact can prevent or resist longitudinal movement of the spacer member along cross post 80 and prevent the formation of gaps between the spacer member and the plates.

It is contemplated that a number of spacer members 240 can be provided in a set having various angles 248 at one or both ends. The surgeon can select the spacer member from the set providing the desired angulation and fit between plates 40, 50 based on pre-operative planning or conditions encountered during surgery.

It is contemplated that any of the spacer member embodiments can be provided in various sizes from which a desired spacer member size and/or shape can be selected by the surgeon. The spacer members can be provided in a kit or as a set, and the spacer member providing the desired outer surface profile and size is selected for placement between the spinous processes based on pre-operative planning or conditions encountered during surgery.

It is further contemplated that the spacer members can be made from a rigid material that positively prevents extension motion of the spinous processes. In another embodiment, the spacer member is made from a compressible material to allow at least limited spinal extension motion between the spinous processes. In still another embodiment, the spacer member is made from an expandable material or is an expandable device that positively directs distraction forces between the spinous processes. In a further embodiment, the spacer member is compressible to initially fit between the spinous processes, and resiliently expands to positively exert a distraction force while yielding under compression forces to allow at least limited spinal extension motion.

In use, the device can be implanted for posterior spinal stabilization as a stand-alone procedure or in conjunction with other procedures. The device can be positioned through a small posterior incision in the patient of sufficient size to admit the device and instrumentation. Following the incision, muscle is moved aside if and as needed for placement of the device into position between spinous processes. After the spacer member is positioned between the spinous processes, the locking member can be loosened if necessary and the plates pushed toward one another with a compression instrument or manually. If spikes are provided, compression is continued until the spikes are sufficiently engaged to the bony material of the spinous processes. The angulation of first plate 30 relative to cross post 80 can be sufficient to enable adaptation of the device to different thicknesses and shapes of the spinal processes of adjacent vertebrae.

Following engagement of plates 30, 50 on the spinal processes, locking member 90 is tightened onto cross post 80 using an appropriate instrument. Locking member 90 may be provided with a break-off portion that provides an indication when sufficient torque is applied. Plates 30, 50 are clamped into engagement with the spinous processes, maintaining the alignment and spacing of the spinous processes while also providing resistance to spinal extension and flexion. The spacer member between the spinous processes can contact and provide support of the adjacent inferior and support spinous process surfaces, resisting settling and compression of the space between the spinous processes. The spacer member can be rigid or stiff so that extension motion is prevented. In another form, the spacer member is resiliently compressible to allow at least limited extension motion. During the implantation procedure, the surgeon can select the shape and size of the spacer member that provides the desired contact or fit with the adjacent spinous processes based on the conditions learned of during pre-operative planning or encountered during surgery.

While the invention has been illustrated and described in detail in the drawings and foregoing description, the same is to be considered as illustrative and not restrictive in character.

All changes and modifications that come within the spirit of the invention are desired to be protected.

What is claimed is:

1. An interspinous implant device comprising:
a first plate having a medial face configured to abut adjacent spinous processes;
a second plate having a medial face configured to abut the adjacent spinous processes; said second plate disposed in spaced relation to said first plate and having a longitudinal plate axis;
the medial face of at least one of the first plate and the second plate comprising a plurality of inwardly projecting projections;
a post connecting the second plate to the first plate and extending along a longitudinal post axis oriented transverse to the medial face of the second plate;
the post pivotable relative to the first plate about a pivot axis; the pivot axis located opposite the second plate with respect to the medial face of the first plate; the pivot axis oriented normal to a theoretical plane disposed generally perpendicular to the medial face of the first plate and containing the longitudinal post axis; the post pivotable about the pivot axis such that the first and second plates may thereby be displaced relative to each other in a direction lying in the theoretical plane and transverse to the post longitudinal axis;
wherein the medial faces of each of the plates extend from the post in opposite directions therefrom between a cephalad end of the respective plate that is positionable along a cephaladly located spinous process and a caudal end of the respective plate positionable along a caudally located spinous process;
the second plate having a first bore; the post extending from the medial face of the first plate through at least a portion of the first bore;
a spacer positioned about the post and disposed between the first and second plates;
a locking mechanism associated with the second plate;
wherein the second plate is moveable along the post toward the first plate and lockable relative thereto via engagement of the locking mechanism with the post.

2. The implant of claim 1 wherein the first plate is configured such that a theoretical line connecting an anterior edge of the cephalad end of the first plate and an anterior edge of the caudal end of the first plate is spaced outwardly from an anterior edge of the first plate proximate the post.

3. The implant of claim 2 wherein the second plate is configured such that a theoretical line connecting an anterior edge of the cephalad end of the second plate and an anterior edge of the caudal end of the second plate is spaced outwardly from an anterior edge of the second plate proximate the first bore.

4. The device of claim 1 wherein the second plate is both moveable along the post toward and away from the first plate and lockable relative thereto via engagement of the locking mechanism with the post at an infinite number of positions along the post.

5. The device of claim 1 wherein the medial faces of at both of the first plate and the second plate comprise a plurality of inwardly projecting projections.

6. The device of claim 5 wherein said plurality of inwardly projecting projections comprises a surface treatment selected from the group consisting of ridges, knurlings, peaks and valleys, teeth, etchings.

7. The device of claim 5 wherein said plurality of inwardly projecting projections comprises an array of inwardly projecting spikes.

8. The device of claim 1:
wherein the cephalad end of the first plate is generally symmetric with the cephalad first end of the second plate and the caudal end of the first plate is generally symmetric with the caudal end of the second plate.

9. The device of claim 1 wherein when the medial face of the first plate is positioned in abutment with a first lateral side of adjacent spinous processes, and the medial face of the second plate is positioned in abutment with a second lateral side of the adjacent spinous processes, the spacer extends between and contacts the adjacent spinous processes.

10. The device of claim 1 wherein the spacer has a cross-section having a generally planar upper surface, a generally planar lower surface, and outwardly facing convex outer sidewalls connecting the upper and lower surfaces.

11. The device of claim 10 wherein the spacer includes at least one outwardly facing concave outer surface for engaging one of the spinous processes.

12. The implant device of claim 1 wherein the post and spacer have interfitting surfaces so that the post is slidably received in a longitudinal passage through the spacer.

13. The device of claim 12 wherein the interfitting surface on the post is a flat surface and the interfitting surface on the spacer is a flat surface along the longitudinal passage.

14. The device of claim 1 wherein:
the first plate has a receptacle; and
the post has a head pivotally received in the receptacle so that the post is pivotal relative to the medial face of the first plate.

15. The device of claim 1 wherein the spacer extends along a central axis between opposite ends thereof, the opposite ends being located adjacent a respective one of the first and second plates, wherein at least one of the opposite ends is angled relative to the other of the opposite ends.

16. The device of claim 1 wherein the spacer includes an outer surface defining a generally rectangular outer surface profile.

17. The device of claim 16 wherein the outer surface includes convexly curved sidewalls and planar upper and lower walls extending between the convexly curved sidewalls.

18. The device of claim 1 wherein the spacer includes an outer surface profile between the plates having a concavely curved central portion between raised ends adjacent respective ones of the plates.

19. The device of claim 1 wherein the spacer is non-rotatably positioned about the post.

20. A method for stabilizing adjacent spinous processes, comprising:
providing an assembly having a first plate, a second plate disposed in spaced relation to the first plate, a post movably connecting the second plate to the first plate and extending along a longitudinal post axis, and a spacer disposed between the first and second plates and about the post;
positioning the first plate along a first side of the adjacent spinous processes such that a medial face of the first plate is oriented toward the spinous processes;
disposing the post;
between the spinous processes so as to extend through a sagittal plane defined thereby
positioning a second plate along a second side of the adjacent spinous processes such that a medial face of the second plate is oriented toward the spinous processes; the second plate having a first bore oriented generally perpendicular to the second plate's medial face;

inserting the post into the first bore in the second plate so that the post axis extends through the first bore;

adjusting the distance between the first and second plates by moving the second plate along the post;

pivoting the post relative to the first plate about a pivot axis to change the relative positions of the first and second plates; the pivot axis located opposite the second plate with respect to the medial face of the first plate; the pivot axis oriented normal to a theoretical plane disposed generally perpendicular to the medial face of the first plate and containing the longitudinal post axis; the pivoting comprising pivoting the post about the pivot axis such that the first and second plates are thereby displaced relative to each other in a direction lying in the theoretical plane and transverse to the post longitudinal axis;

locking the second plate relative to the post so as to secure the second plate along the post in spaced relation to the first plate.

21. The method of claim 20 further comprising selecting a spacer from a set of spacers, the selected spacer providing a desired fit between the spinous processes.

* * * * *

UNITED STATES PATENT AND TRADEMARK OFFICE
CERTIFICATE OF CORRECTION

| | | |
|---|---|---|
| PATENT NO. | : 7,727,233 B2 | Page 1 of 1 |
| APPLICATION NO. | : 11/117809 | |
| DATED | : June 1, 2010 | |
| INVENTOR(S) | : Blackwell et al. | |

It is certified that error appears in the above-identified patent and that said Letters Patent is hereby corrected as shown below:

On the Cover Page, item (73), under "Assignee", in Column 1, Line 1, delete "Inc." and insert -- Inc. (U.S.) --, therefor.

In Column 7, Line 58, in Claim 5, delete "at both" and insert -- both --, therefor.

In Column 8, Line 19, in Claim 12, delete "implant device" and insert -- device --, therefor.

In Column 8, Lines 60-61, in Claim 20, delete "post; between" and insert -- post between --, therefor.

In Column 8, Line 62, in Claim 20, delete "thereby" and insert -- thereby; --, therefor.

Signed and Sealed this
Sixteenth Day of August, 2011

David J. Kappos
*Director of the United States Patent and Trademark Office*